(12) United States Patent
Grashow et al.

(10) Patent No.: US 10,758,697 B2
(45) Date of Patent: Sep. 1, 2020

(54) ADAPTIVE BUCKLING MEMBER IN A PATIENT INTERFACE

(71) Applicant: KONINKLIJKE PHILIPS N.V., Eindhoven (NL)

(72) Inventors: Jonathan Sayer Grashow, Cheswick, PA (US); Robert O'Grady, Pittsburgh, PA (US); Robert William Baiko, Pittsburgh, PA (US); Lauren Patricia Chodkowski, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 443 days.

(21) Appl. No.: 15/535,422

(22) PCT Filed: Dec. 10, 2015

(86) PCT No.: PCT/IB2015/059509
§ 371 (c)(1),
(2) Date: Jun. 13, 2017

(87) PCT Pub. No.: WO2016/097948
PCT Pub. Date: Jun. 23, 2016

(65) Prior Publication Data
US 2017/0368286 A1 Dec. 28, 2017

Related U.S. Application Data

(60) Provisional application No. 62/093,843, filed on Dec. 18, 2014.

(51) Int. Cl.
*A61M 16/06* (2006.01)

(52) U.S. Cl.
CPC .... *A61M 16/0611* (2014.02); *A61M 16/0616* (2014.02); *A61M 16/0666* (2013.01); *A61M 16/0683* (2013.01)

(58) Field of Classification Search
CPC .......... A61M 16/0611; A61M 16/0616; A61M 16/0683; A61M 16/0666; A61M 16/0622; A61M 16/0816; A61M 16/0605
See application file for complete search history.

(56) References Cited

U.S. PATENT DOCUMENTS

| 8,051,855 | B2 | 11/2011 | Busch et al. |
| 2002/0013407 | A1 | 1/2002 | Pearce |
| | | (Continued) | |

FOREIGN PATENT DOCUMENTS

| CN | 101455871 A | 6/2009 |
| CN | 102371020 A | 3/2012 |
| | (Continued) | |

*Primary Examiner* — Samchuan C Yao
*Assistant Examiner* — Margaret M Luarca
(74) *Attorney, Agent, or Firm* — Michael W. Haas

(57) ABSTRACT

A wearable device (8,60,70,86) structured to exert a contact pressure between the wearable device and a skin surface of a wearer, such as a patient interface device for delivering a flow of breathing gas to a patient, includes a first member (18,72,96), such as a faceplate member, structured to have a first pressure applied thereto, a contact member (14,74), such as a sealing cushion, structured to exert the contact pressure against the skin surface in response to the first pressure, and a support member (20,62,78) positioned between the first member and the contact member, the support member including a plurality of compression members (40,52,54,64,84), wherein each of the compression members is structured to buckle in response to a compression force having at least a first predetermined level being applied to the support member.

11 Claims, 13 Drawing Sheets

(56) References Cited

U.S. PATENT DOCUMENTS

| | | | |
|---|---|---|---|
| 2006/0207599 A1* | 9/2006 | Busch | A61M 16/06 128/206.24 |
| 2008/0230068 A1 | 9/2008 | Rudolph | |
| 2008/0257354 A1 | 10/2008 | Davidson | |
| 2012/0297526 A1 | 11/2012 | Leon | |
| 2013/0133664 A1* | 5/2013 | Startare | A61M 16/06 128/206.24 |
| 2013/0146060 A1* | 6/2013 | Ho | A61M 16/06 128/205.25 |
| 2014/0068840 A1 | 3/2014 | Nauman | |

FOREIGN PATENT DOCUMENTS

| | | |
|---|---|---|
| EP | 1042759 B1 | 9/2011 |
| WO | WO2005123166 A1 | 12/2005 |
| WO | WO2009062265 A1 | 5/2009 |
| WO | WO2012025843 A1 | 3/2012 |
| WO | WO2013171617 A2 | 11/2013 |

\* cited by examiner

ADAPTIVE BUCKLING MEMBER IN A PATIENT INTERFACE

CROSS-REFERENCE TO RELATED APPLICATIONS

This patent application claims the priority benefit under 35 U.S.C. § 371 of international patent application No. PCT/ID2015/059509, filed Dec. 10, 2015, which claims the priority benefit under 35 U.S.C. § 119(e) of U.S. Provisional Application No. 62/093,843 filed on Dec. 18, 2014, the contents of which are herein incorporated by reference.

BACKGROUND OF THE INVENTION

1. Field of the Invention

The present invention pertains to wearable devices, such as, without limitation, patient interface devices structured to deliver a flow of breathing gas to a patient, and, in particular, to wearable devices, such as patient interface devices, employing a support member structured to provide adaptive buckling to improve wearer fit and comfort.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, a nasal cushion that rests beneath the patient's nose (such as a "pillows" style nasal cushion having nasal prongs that are received within the patient's nares or a "cradle" style nasal cushion that rests beneath and covers the patient's nares), or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient.

It is known to maintain such devices on the face of a wearer by a headgear having one or more straps adapted to fit over/around the patient's head. The headgear typically wraps around the patient's head in order to apply the necessary forces normal to the face to achieve a suitable seal.

Over tightening of mask headgear straps frequently occurs during therapy such as OSA therapy. Over tightening is undesirable as it typically causes discomfort, facial red marks, pressure sores and/or open wounds. As a result, over tightening can have a tremendously negative effect on compliance with therapy as patients will be reluctant to use the mask as often and/or for as long as directed. The importance of therapy compliance is increasing, as insurance and Medicare guidelines are now requiring the industry to prove compliance for their patient populations.

SUMMARY OF THE INVENTION

In one embodiment, a wearable device structured to exert a contact pressure between the wearable device and a skin surface of a wearer, such as a patient interface device, is provided. The wearable device includes a first member, such as a face plate member, structured to have a first pressure applied thereto, a contact member, such as a sealing cushion, structured to exert the contact pressure against the skin surface in response to the first pressure, and a support member positioned between the first member and the contact member, the support member including a plurality of compression members, wherein each of the compression members is structured to buckle in response to a compression force having at least a first predetermined level being applied to the support member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
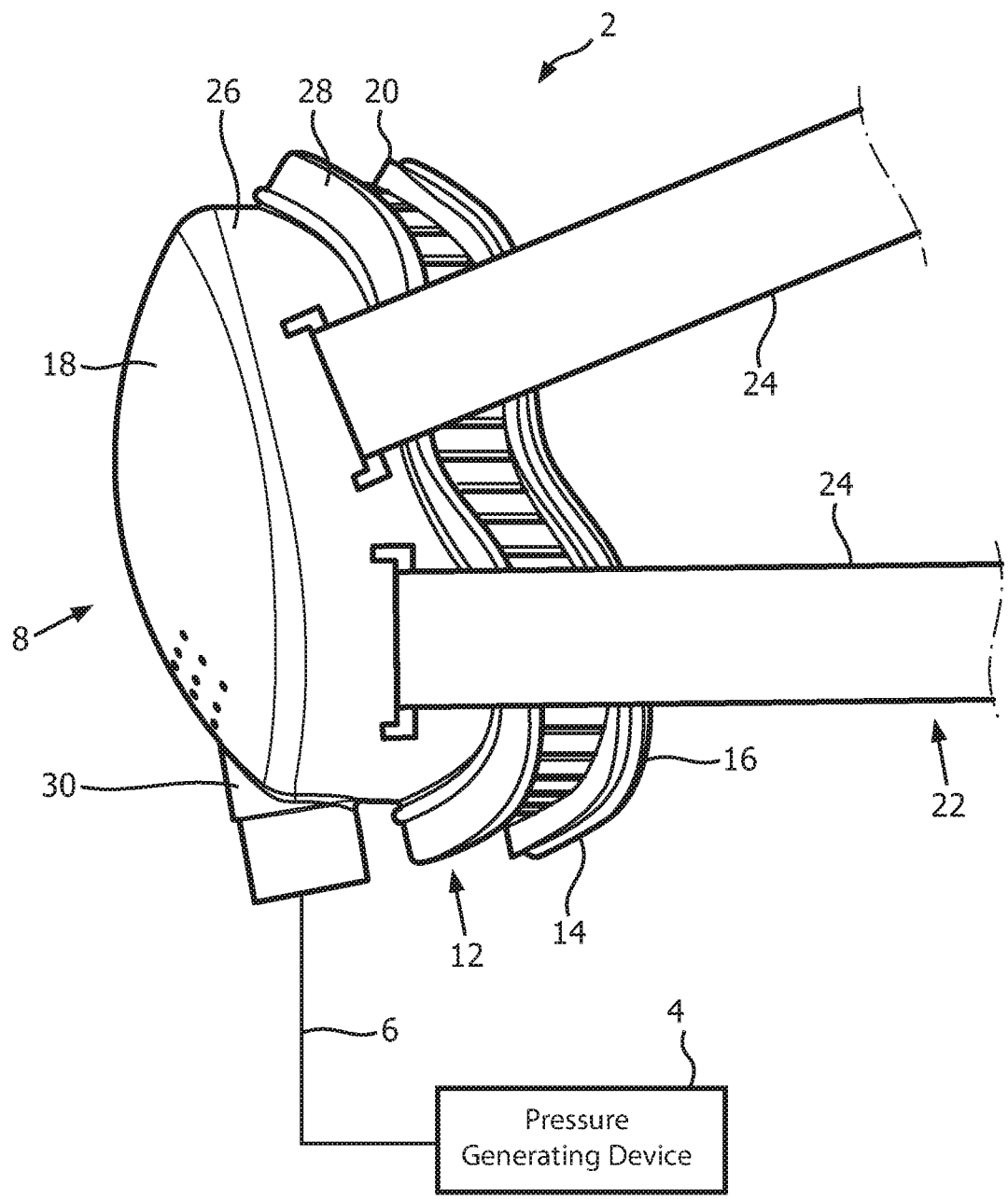
FIG. 1 is a schematic diagram of a system adapted to provide a regimen of respiratory therapy to a patient according to one exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "buckling" shall mean a structural failure mode which occurs when a relatively tall/thin structural member is compressed and lateral instabilities caused the structural member to suddenly bend. The force at which a structural member starts to buckle is a function of the geometry and material of the structural member.

As used herein, the term "elastomeric material" shall mean a material that exhibits elastic but not viscous characteristics when undergoing deformation, and, as a result, does not exhibit time dependent strain. Thus, the term "elastomeric material" as used herein refers to a material that deforms under the influence of an applied stress and returns instantaneously to its original state once the stress is removed, thereby recovering from substantially all of the deformation. As used herein, the terms "instantaneous" and "instantaneously" shall mean occurring with almost no delay; completed within a moment or an instant; immediate.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIG. 1. System 2 includes a pressure generating device 4, a delivery conduit 6, and a patient interface device 8. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are often collectively referred to as a patient circuit.

Figure 2:
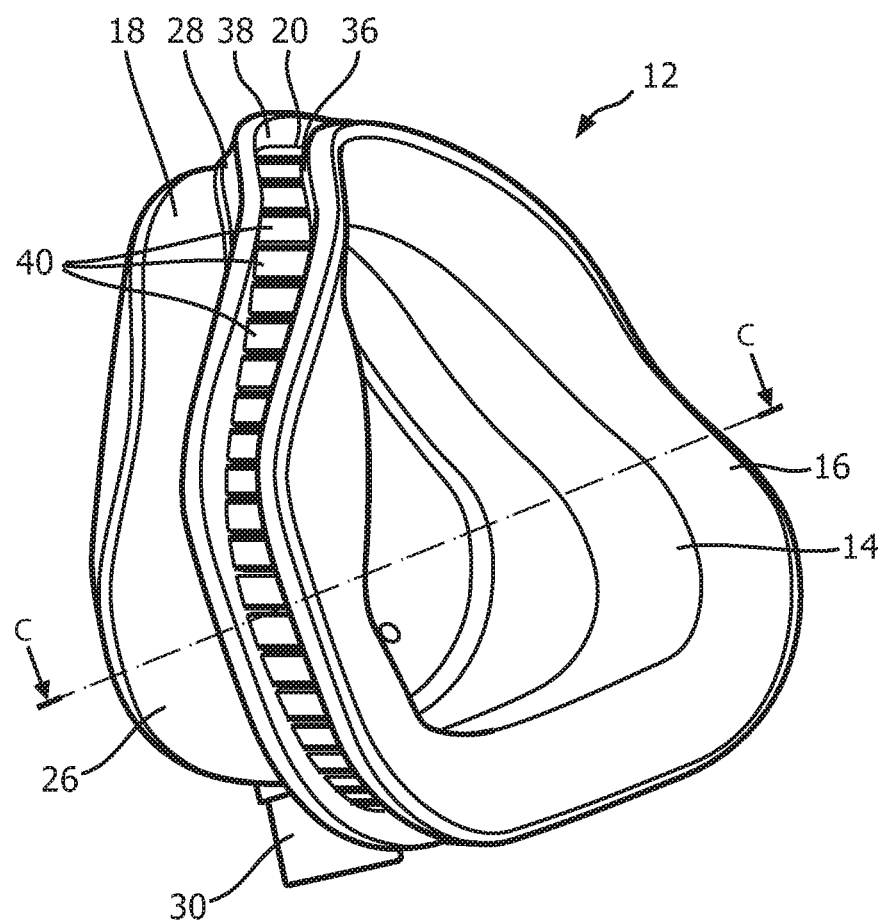
FIG. 2 is an isometric view.
Figure 3:
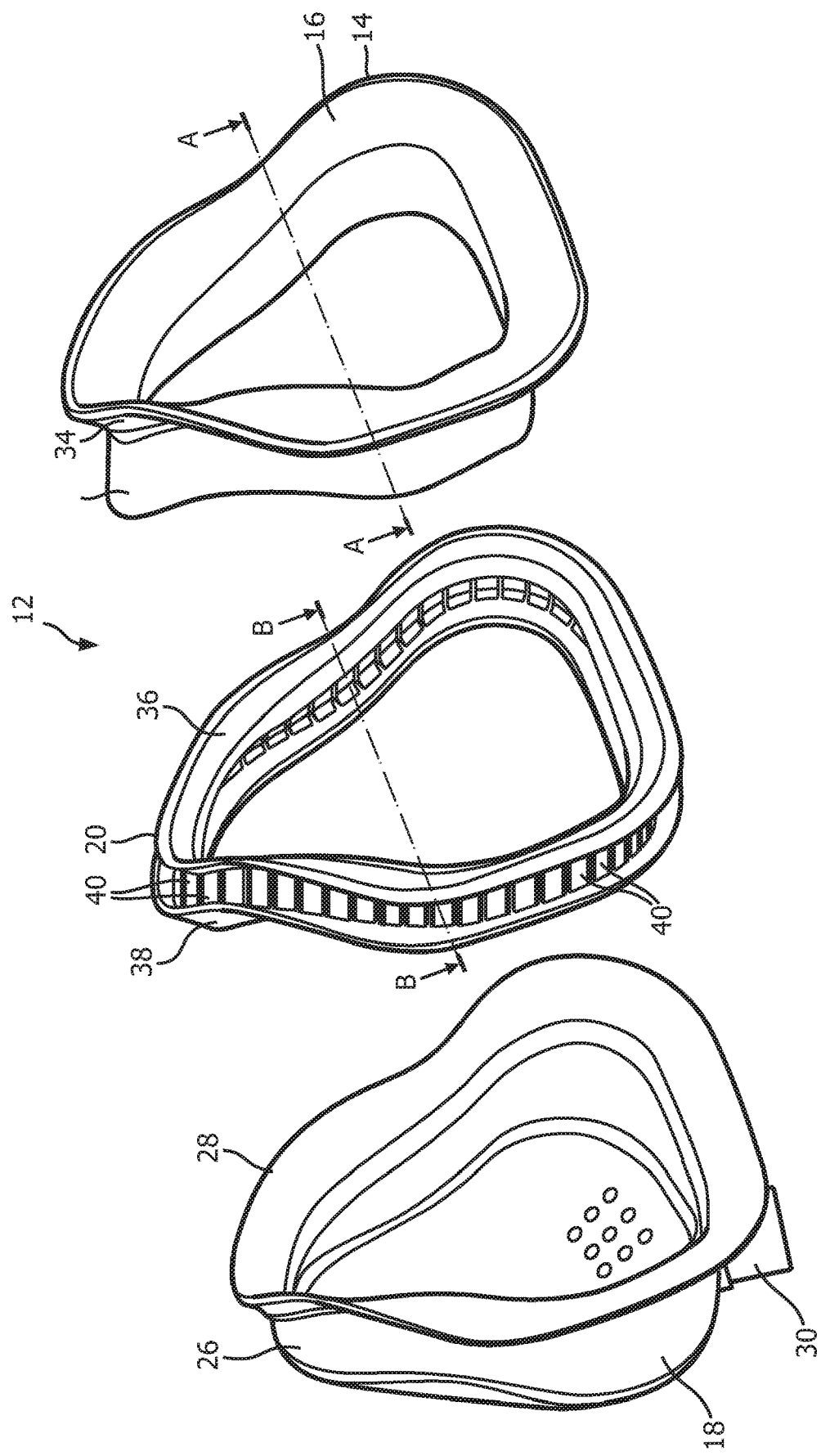
FIG. 3 is an exploded-isometric view of a patient sealing assembly of a patient interface device forming a part of the system of FIG. 1 according to an exemplary embodiment.

As seen in FIG. 1, patient interface 8 includes a patient sealing assembly 12, which in the illustrated embodiment is a nasal/oral mask. However, other types of patient sealing assemblies, such as, without limitation, a nasal mask, a nasal cushion (e.g., "pillows" or "cradle" style), or a full face mask, which facilitate the delivery of the flow of breathing gas to the airway of a patient may be substituted for patient sealing assembly 12 while remaining within the scope of the present invention. FIG. 2 is an isometric view, and FIG. 3 is an exploded-isometric view of patient sealing assembly 12 according to an exemplary embodiment. Patient sealing assembly 12 includes: (i) a sealing cushion 14 having a sealing flap 16, (ii) a faceplate member 18 coupled to sealing cushion 14 at the end of sealing cushion 14 opposite sealing flap 16, and (iii) a support member 20 provided in between faceplate member 18 and sealing flap 16. The structure of each of sealing cushion 14, faceplate member 18, and support member 20 is described in greater detail herein. Patient interface device 8 also includes a headgear component 22 (FIG. 1) including a plurality of straps 24 for securing patient interface device 8 to the patient's head (at loop members 25 extending from faceplate number 18).

As seen in FIGS. 1-3, faceplate member 18 includes a generally triangularly shaped main body portion 26 having a flange 28 extending around the perimeter of the rear side thereof. Flange 28 defines a rear opening of faceplate member 18, and is contoured in a manner designed to generally match the facial surface and geometry of a wearer of patient interface device 8. Faceplate member 18 includes an integral fluid coupling conduit 30 extending from and fluidly coupled to main body portion 26. In use, delivery conduit 6 is coupled to coupling conduit 30, and thus coupling conduit 30 is the mechanism by which breathing gas is delivered to patient interface device 8 from pressure generating device 4. In the exemplary embodiment, faceplate member 18 is made of a rigid or semi-rigid material, such as, without limitation, polycarbonate, an injection molded thermoplastic, or silicone.

Figure 4:
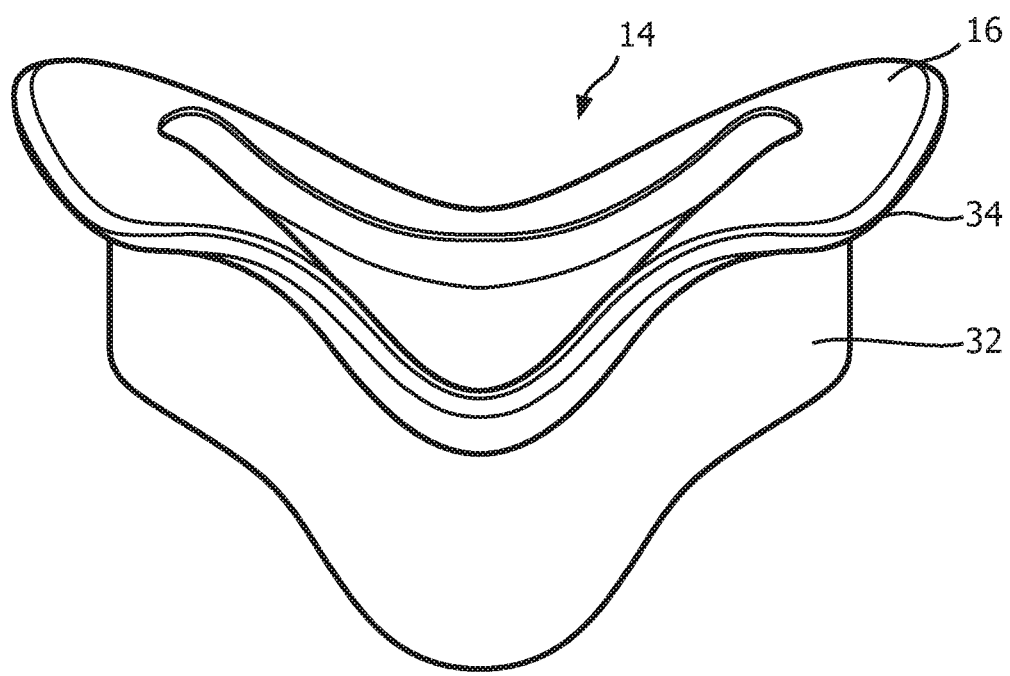
FIG. 4 is a top elevational view of a sealing cushion forming a part of the patient interface device of FIGS. 2 and 3 according to the exemplary embodiment.
Figure 5:
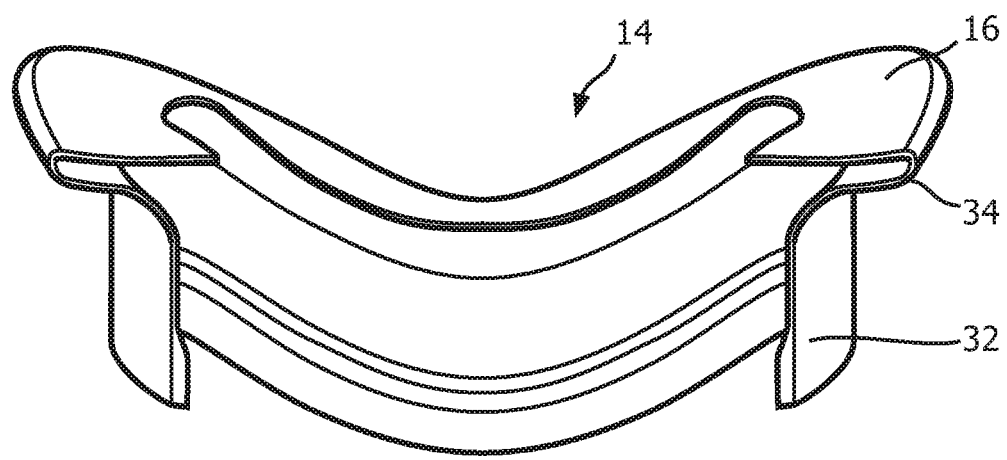
FIG. 5 is a cross-sectional view of the sealing cushion of FIG. 4 taken along lines A-A of FIG. 3.

FIG. 4 is a top elevational view of sealing cushion 14 according to the exemplary embodiment. FIG. 5 is a cross-sectional view of sealing cushion 14 taken along lines A-A of FIG. 3. In the illustrated embodiment, sealing cushion 14 is defined from a unitary piece of soft, flexible, cushiony material, such as, without limitation, silicone, an appropriately soft thermoplastic elastomer, a closed cell foam, or any combination of such materials. Sealing cushion 14 includes a lower support portion 32 that is structured to be attached to an interior of main body portion 26 of faceplate member 18, and an upper support portion 34 coupled, to the distal end of lower support portion. Sealing flap 16 is coupled to the distal end of upper support portion 34. Sealing flap 16 is contoured in a manner designed to generally match the facial surface and geometry of the wearer of patient interface device 8, and is structured and configured to engage and make a substantially fluid tight seal against the face of the wearer of patient interface device 8.

Figure 6:
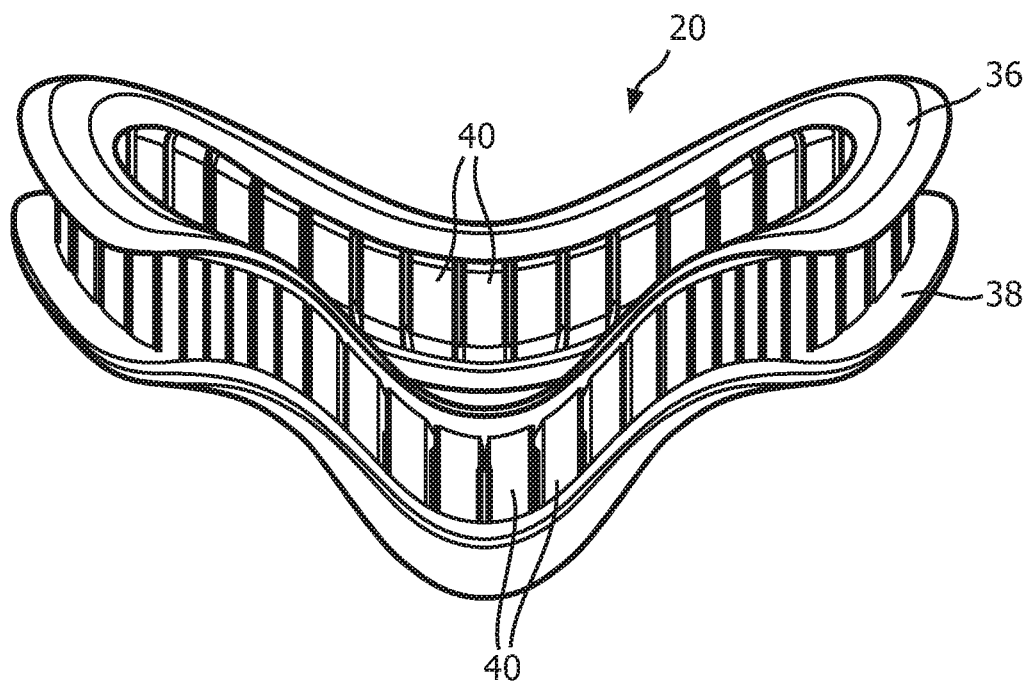
FIG. 6 is a top elevational view of a support member forming a part of the patient interface device of FIGS. 2 and 3 according to the exemplary embodiment.
Figure 7:
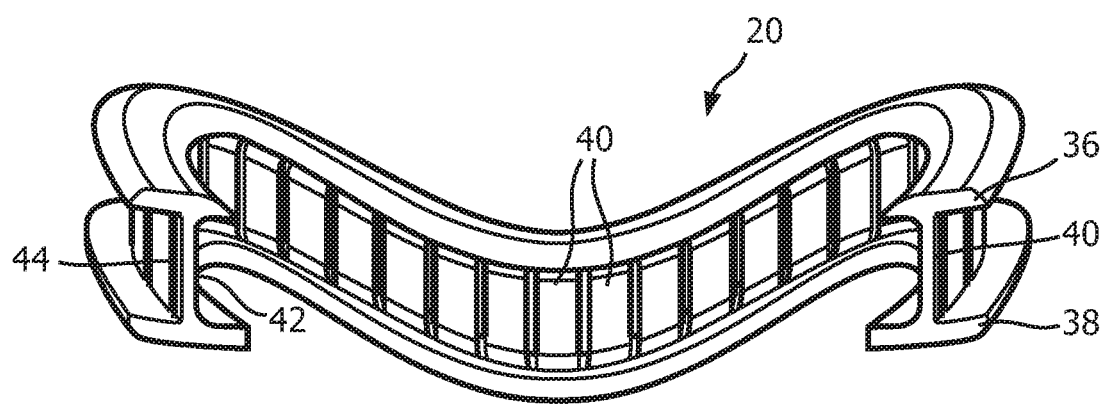
FIG. 7 is a cross-sectional view of the support member of FIG. 6 taken along lines B-B of FIG. 3.

FIG. 6 is a top elevational view of a support member 20 according to the exemplary embodiment. FIG. 7 is a cross-sectional view of a support member 20 taken along lines B-B of FIG. 3. In the illustrated embodiment, support member 20 is defined from a unitary piece of flexible, resilient elastomeric material, such as, without limitation, silicone, a closed cell foam, or any combination of such materials. In the non-limiting illustrated exemplary embodiment, support member 20 includes a top flange 36, a bottom flange 38, and a plurality of compression members 40. As seen in FIGS. 6 and 7, each compression member 40 extends from top flange 36 to bottom flange 38. Top flange 36 and bottom flange 38 are contoured in a manner designed to generally match the facial surface and geometry of the wearer of patient interface device 8. As described in greater detail herein, each of the compression members 40 is structured and configured to buckle when a compressive force is applied to patient interface device 8 (e.g., by the tightening of straps 24 of headgear component 22) in a direction that is substantially parallel to the longitudinal axis of each of the compression members 40.

Figure 8:
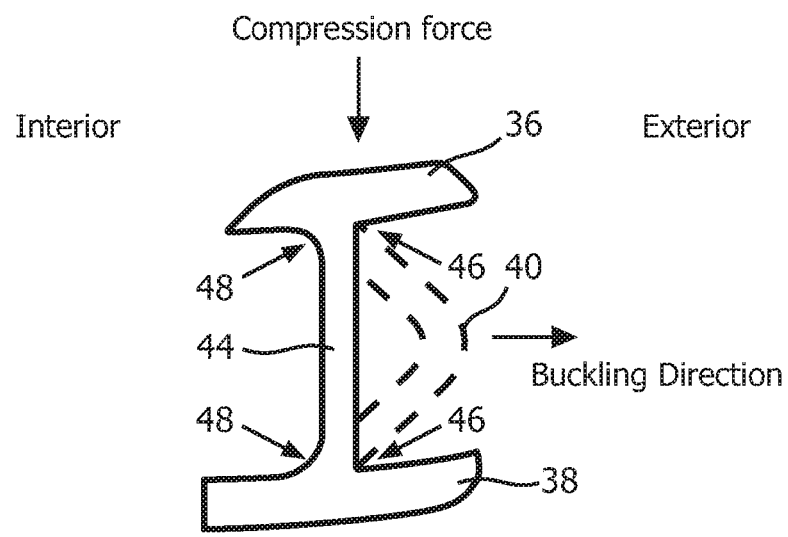
FIG. 8, which is a schematic representation of the cross sectional surface of a support member taken at the middle thereof.

In addition, as seen in FIG. 7, compression members 40 define in interior surface 42 and an exterior surface 44 of support member 20. As seen in FIG. 8, which is a schematic representation of the cross sectional surface of support member 20 taken at the middle of any of the support members 40, support member 20 includes orthogonal or square interconnection points 46 between each compression member 40 and top flange 36 and bottom flange 38 at the exterior surface 44, and rounded interconnection points 48 between each compression member 40 and top flange 36 and bottom flange 38 at the interior surface 42. Such a configuration will bias compression members 40 to buckle in a direction toward the exterior of support member 20 is shown by the arrow in FIG. 8 when subjected to a compression force that is above a certain threshold level. The significance of this buckling direction is described elsewhere herein.

Figure 9:
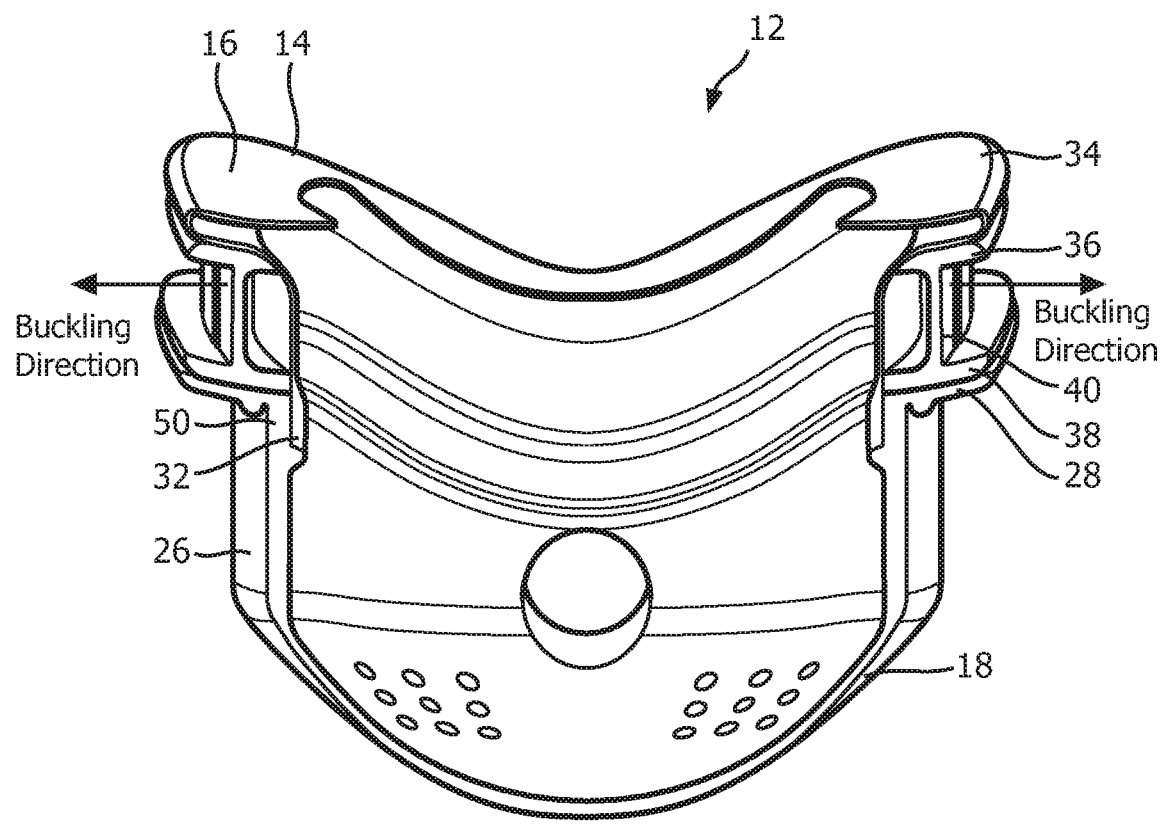
FIG. 9 which is a cross-sectional view of the patient sealing assembly of FIGS. 2 and 3 taken along lines C-C of FIG. 2.

As seen in FIG. 2 and FIG. 9, which is a cross-sectional view of patient sealing assembly 12 taken along lines C-C of FIG. 2, when patient sealing assembly 12 is assembled, support member 20 is positioned between flange 28 of faceplate member 18 and upper support portion 34 and sealing flap 16 of sealing cushion 14. In particular, bottom flange 38 of support member 20 engages and rests against flange 28 of frame member 18 and top flange 36 of support member 20 engages and rests against the upper support portion 34 of sealing cushion 14. As seen in FIG. 9, lower support portion 32 of sealing cushion 14 is fixedly attached to main body portion 26 of faceplate member 18 at an upper portion 50 thereof. Attachment at this point may be accomplished by any of a number of mechanisms, such as, without limitation, using an adhesive or by over molding faceplate member 18 and sealing cushion 14 during production. In addition, in the non-limiting, illustrated embodiment, support member 20 is not fixedly attached to either faceplate member 18 or sealing cushion 14, but instead "floats" in between those 2 components. In an alternative embodiment, bottom flange 38 may be fixedly attached to flange 28 such as by an adhesive or over molding.

During use, support member 20 functions to act as an adaptive buckling mechanism that buckles when a desired contact pressure against the face (applied by, for example, straps 24 of headgear component 20) is reached. More specifically, as such a strapping force is applied, support member 20 will be compressed in a direction that is parallel to the longitudinal axis of each of the compression members 40, and each compression member 40 will buckle as shown in FIG. 8 toward the exterior of support member 20 when a certain, predefined contact pressure has been achieved. In the exemplary embodiment, the geometry and/or material of each compression member 40 is chosen such that a desired contact pressure will be exerted against the proximal surface of the face when each of the compression members 40 undergo buckling as just described. As noted elsewhere herein, the nature of square interconnection points 46 and rounded interconnection points 48 causes compression members 40 to be biased to buckle in a direction toward the exterior of patient interface device 8 and away from the interior of patient interface device 8. This feature ensures that compression members 40 will not undesirably engage lower support portion 32 of sealing cushion 14 when buckled.

Thus, the disclosed concept provides a patient interface device 8 that prevents undesirable over tightening, which can lead to red marks and pressure sores, by including an adaptive buckling support member 20 structured to buckle when a desired contact pressure has been reached. Such a structure allows patient interface device 8 to conform to the wearer's face without creating undesirable pressure points and local protrusions. Such a configuration also prevents deformations in one area of patient interface device 8 from influencing the geometry in other areas of patient interface device 8, which can result in wrinkling and/or other undesirable structure structural deformations in components such as, without limitation, sealing member 14.

Figure 10:
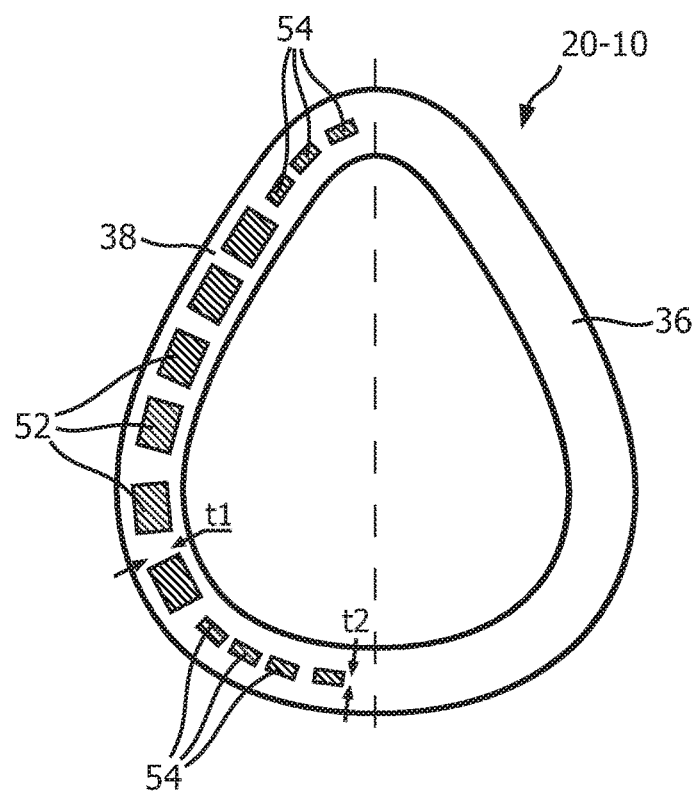
FIGS. 10-13 are schematic diagrams, in partial cross-section, of alternative support members according to various alternative exemplary embodiments that may be used in the sealing assembly of FIGS. 2 and 3.

FIG. 10 is a schematic diagram, in partial cross-section, of an alternative support member 20-10 according to an alternative exemplary embodiment. Support member 20-10 is similar to support member 20 described elsewhere herein, and may be used as a substitute therefor. As seen in FIG. 10, support member 20-10 includes top flange 36 and bottom flange 38 as described elsewhere herein. Support member 20-10 differs from support member 20 in that it includes alternative compression members 52 at the side regions thereof, and alternative compression members 54 at the apex and bottom regions thereof. Compression members 52 and 54 are similar in structure to compression members 40 described herein, except that compression members 52 and 54 have different thicknesses in the plane that is normal to the longitudinal axis thereof. In particular, compression members 52 have a first thickness $t1$ and compression members 54 have a second thickness $t2$, wherein $t1>t2$. The thicknesses $t1$ and $t2$ of compression members 52, 54 will, among other factors, control the contact pressure at which compression members 52, 54 will buckle (i.e., the greater the thickness, the greater the contact pressure required for buckling). Thus, the configuration shown in FIG. 10 provides a support member 20-10 wherein the contact pressure which will produce buckling will vary depending upon the location around the perimeter thereof that is in question. In the illustrated embodiment, the contact pressure required for buckling will be greater at the side regions than at the apex and bottom regions.

Figure 11:
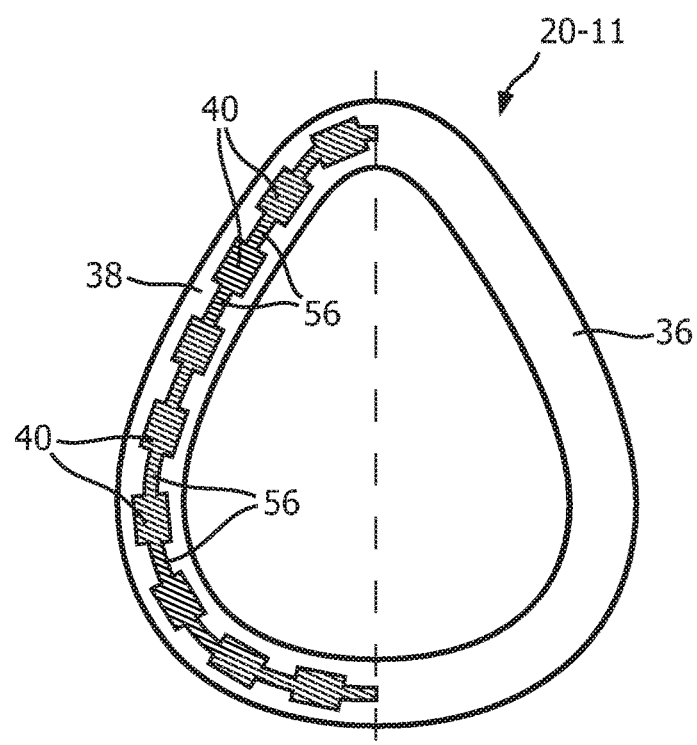

FIG. 11 is a schematic diagram, in partial cross-section, of an alternative support member 20-11 according to another alternative exemplary embodiment. Support member 20-11 is similar to support member 20 described elsewhere herein, and may be used as a substitute therefor. As seen in FIG. 11, support member 20-11 includes top flange 36, bottom flange 38 and compression members 40 as described elsewhere herein. Support member 20-11 differs from support member 20 in that it further includes air-tight webbing members 56, wherein each webbing member 56 is provided between in adjacent pair of compression members 40. Webbing members 56 may thus be used in applications wherein it is necessary for compression member 20-11 to be air-tight. In the exemplary embodiment, the thickness and/or durometer of webbing members 56 may be reduced as compared to the thickness and/or durometer of compression members 42 minimize the coupling between compression members 40 in order to allow compression members 42 buckle independently.

As will be appreciated, support member 20-11 having compression members 40 and webbing members 56 of different durometers may be formed by an over molding process or may be formed independently and then adhered to one another.

Figure 12:
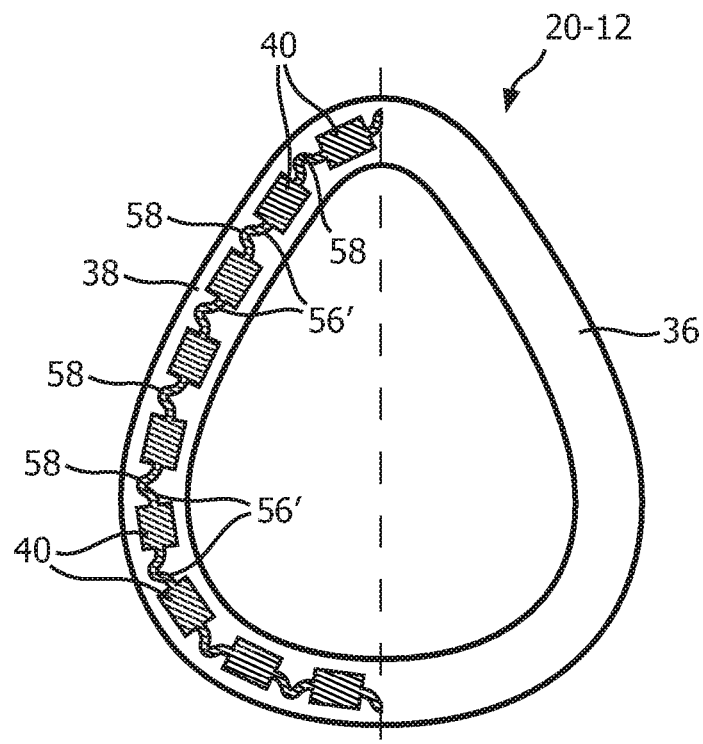

FIG. 12 is a schematic diagram, in partial cross-section, of a further alternative support member 20-12 according to another alternative exemplary embodiment. Support member 20-12 is similar to support member 20-11 just described, except that it includes alternative webbing members 56' which, rather than being generally linear, each have a bent shape including an angled portion 58. Such a configuration of webbing members 56 further decreases the coupling between compression members 40.

Figure 13:
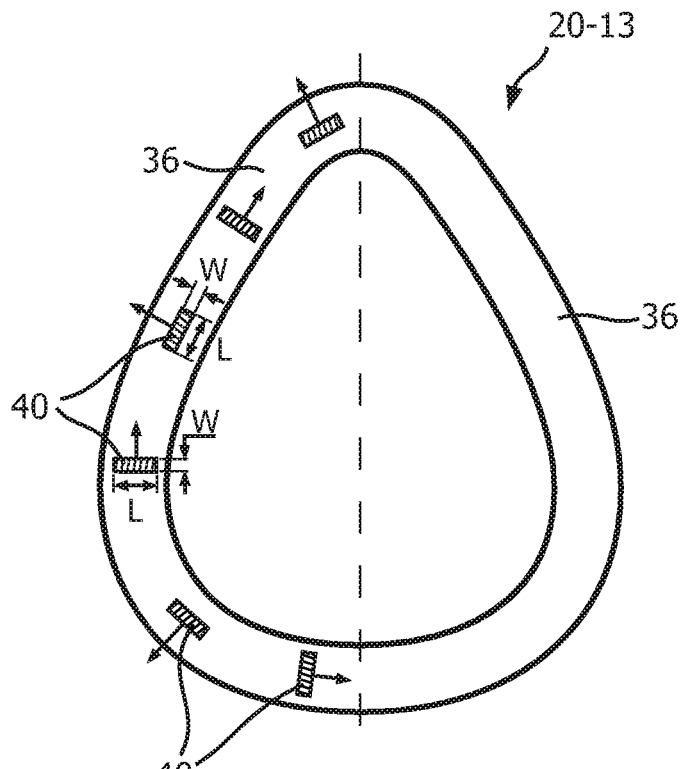

FIG. 13 is a schematic diagram, in partial cross-section, of an alternative support member 20-13 according to still another alternative exemplary embodiment. Support member 20-13 is similar to support member 20 described elsewhere herein, and may be used as a substitute therefor. As seen in FIG. 13, support member 20-13 includes top flange 36, bottom flange 38 and compression members 40. As also seen in FIG. 13, each compression member 40 includes a thickness or width dimension W and a length dimension L that each lie in a plane that is normal to the longitudinal axis of the compression member 40. Support member 20-13 differs from support member 20 in that certain of the compression members 40 have a length dimension L that extends in a direction that is substantially perpendicular to a line tangent to the outer perimeter of support member 20-13 at that compression member 40, and certain of the compression members 40 have a length dimension L that extends in a direction that is substantially parallel to a line tangent to the outer perimeter of support member 20-13 at that compression member 40. Such a configuration will result in compression members 40 having differing (and thus controlled) buckling directions as shown by the arrows in FIG. 13, with each buckling direction being determined by the orientation of the compression member 40 in question. This configuration will in turn help to prevent undesired shearing of compression members 40. In the exemplary embodiment, compression members 40 are spaced apart from one another such that they do not contact one another when fully buckled.

Figure 14:
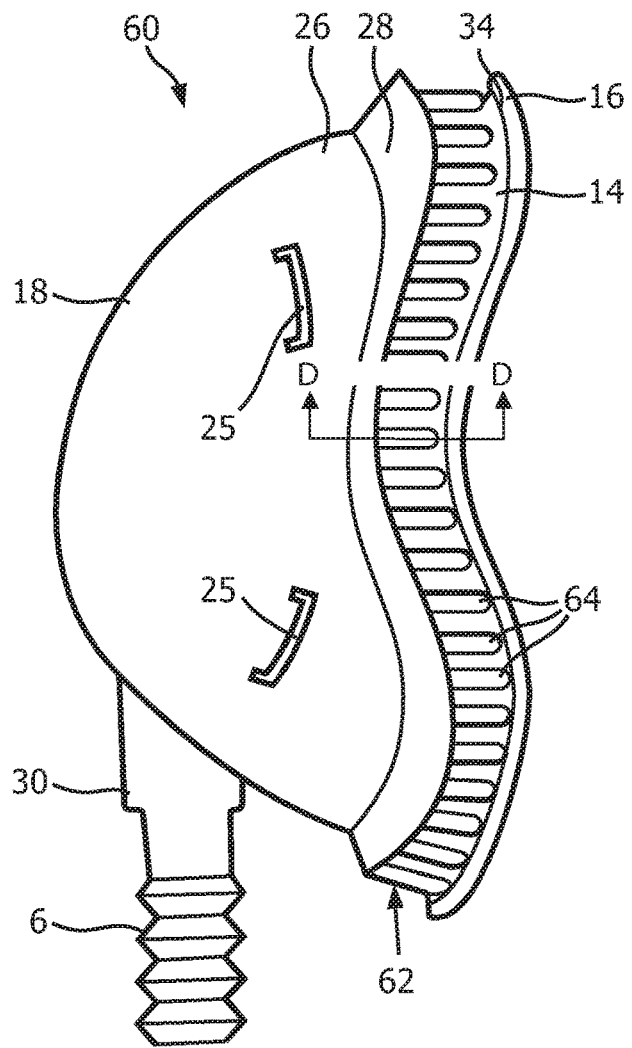
FIG. 14 is a schematic diagram of a patient interface device according to an alternative exemplary embodiment.
Figures 15, 16:
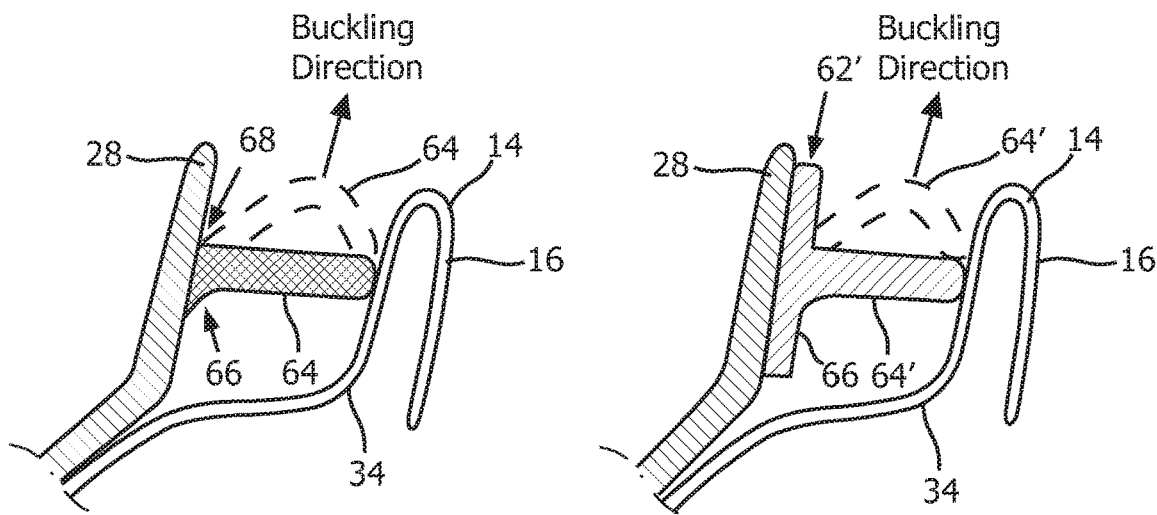
FIG. 15 is a cross-sectional view of the patient interface device of FIG. 14 taken along lines D-D.
FIG. 16 is a cross-sectional view of a variation of the patient interface device shown in FIG. 14.

FIG. 14 is a side view of a patient interface device 60 according to an alternative exemplary embodiment of the disclosed concept. Patient interface device 60 is similar to patient interface device 8 described elsewhere herein, and like components are labeled with like reference numerals. Patient interface device 60 is different from patient interface device 8 in that it includes an alternative support system 62 provided between flange 28 and upper support portion 34 of sealing cushion 14 that comprises a plurality of individual compression members 64 that are each attached to the underside of flange 28 of base plate member 18. This configuration is shown in FIG. 15, which is a cross-sectional view taken along lines D-D of FIG. 14. As seen in FIG. 15, each compression member 64 includes an inner rounded connection point 66 and an outer square connection point 68 where the compression member 64 is attached to flange 28. These features will bias each compression member 64 to buckle in the buckling direction shown in FIG. 15 toward the outside of patient interface device 60. In a further alternative embodiment, as seen in FIG. 16, support system 62 may be formed as a unitary member (labeled 62' in FIG. 16) having a bottom flange 66 to which a plurality of compression members 64' are attached).

Figure 17:
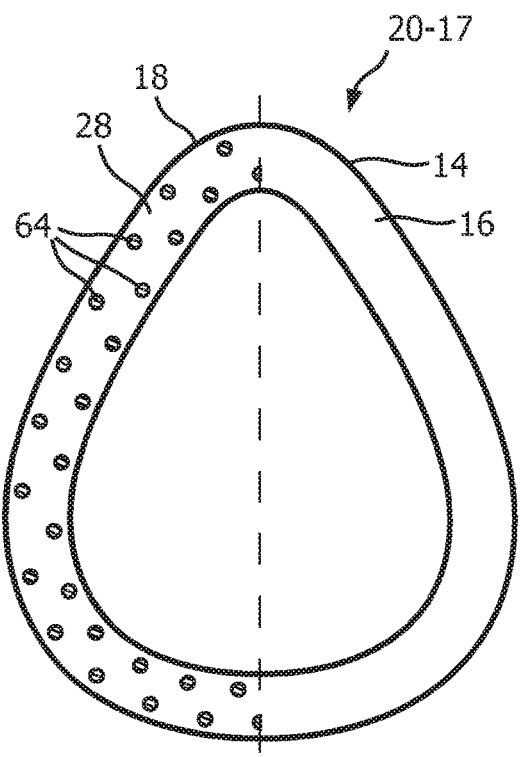
FIG. 17 is a schematic view, in partial cross-section, of an alternative sealing assembly that may be used in the patient interface device of FIG. 14.

FIG. 17 is a schematic diagram, in partial cross section, of an alternative patient interface device 60-17 that is similar to patient interface device 60 described above, except that in this embodiment the compression members 64 are staggered along the underside of flange 28 of phase plate member 18.

Figure 18:
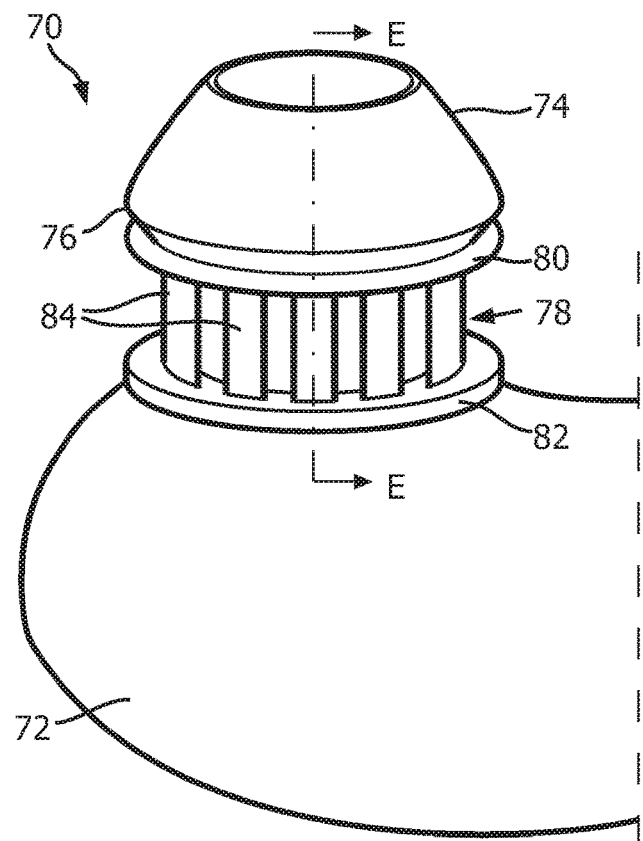
FIGS. 18 and 19 are front and cross-sectional views, respectively, of a sealing assembly according to a further alternative exemplary embodiment.
Figure 19:
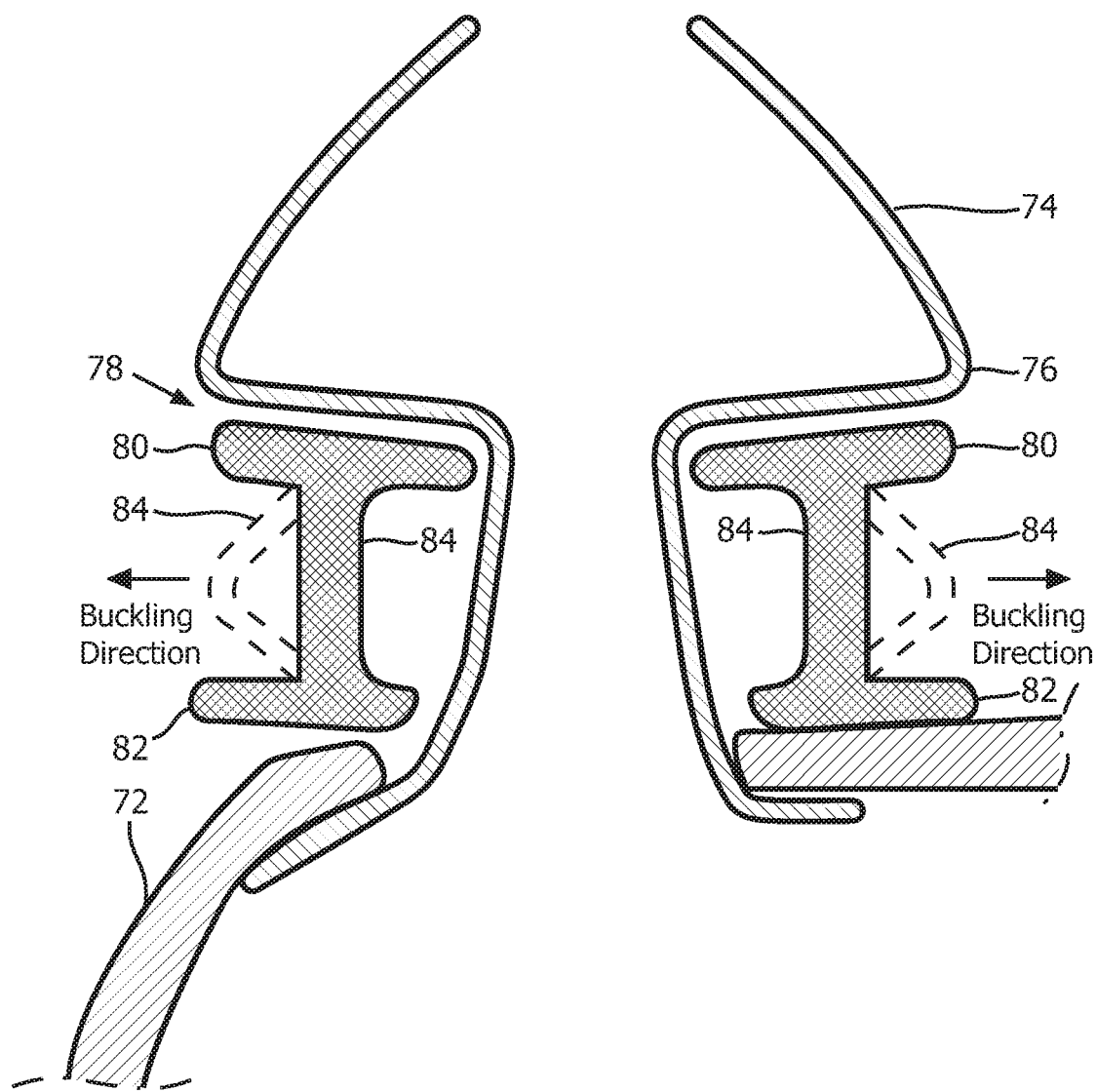

FIG. 18 is a schematic diagram of a sealing assembly 70 according to still another alternative exemplary embodiment of the disclosed concept. FIG. 19 is a cross-sectional view of sealing assembly 70 taken along lines E-E in FIG. 18. Sealing assembly 70 shown in FIGS. 18 and 19 is a pillows style nasal cushion. Sealing assembly 70 includes: (i) a main body portion 72 structured to receive a flow of breathing gas from, for example, a pressure generating device like pressure generating device 4, (ii) a nasal prong member 74 (which is one of a pair of such nasal prong members) that is fixedly coupled to main body portion 72 by, for example and without limitation, an adhesive, and (iii) a support member 78 provided between a bottom flange 76 of nasal prong member 74 and a top portion of the body portion 72. Main body portion 72 and nasal prong member 74 are each made of a soft, flexible, cushiony material, such as, without limitation, silicone, an appropriately soft thermoplastic elastomer, a closed cell foam, or any combination of such material, and support member 78 is defined from a unitary piece of flexible, resilient elastomeric material, such as, without limitation, silicone, a closed cell foam, or any combination of such materials.

In the non-limiting illustrated exemplary embodiment, support member 78 includes a top flange 80, a bottom flange 82, and a plurality of compression members 84. As seen in FIGS. 18 and 19, each compression member 84 extends from top flange 80 to bottom flange 82. In addition, each of the compression members 84 is structured and configured to buckle when a compressive force is applied to patient interface device 70 (e.g., by the tightening of the straps of a headgear component used there with) in a direction that is substantially parallel to the longitudinal axis of each of the compression members 84.

In addition, as seen in FIG. 19, compression members 84 define in interior surface and an exterior surface of support member 84, and support member 78 includes orthogonal or square interconnection points between each compression member 84 and top flange 80 and bottom flange 82 at the exterior surface, and rounded interconnection points between each compression member 84 and top flange 80 and bottom flange 82 at the interior surface. Such a configuration will bias compression members 84 to buckle in a direction toward the exterior of support member 78 (and away from nasal prong 74) when subjected to a compression force that is above a certain threshold level.

Figure 20:
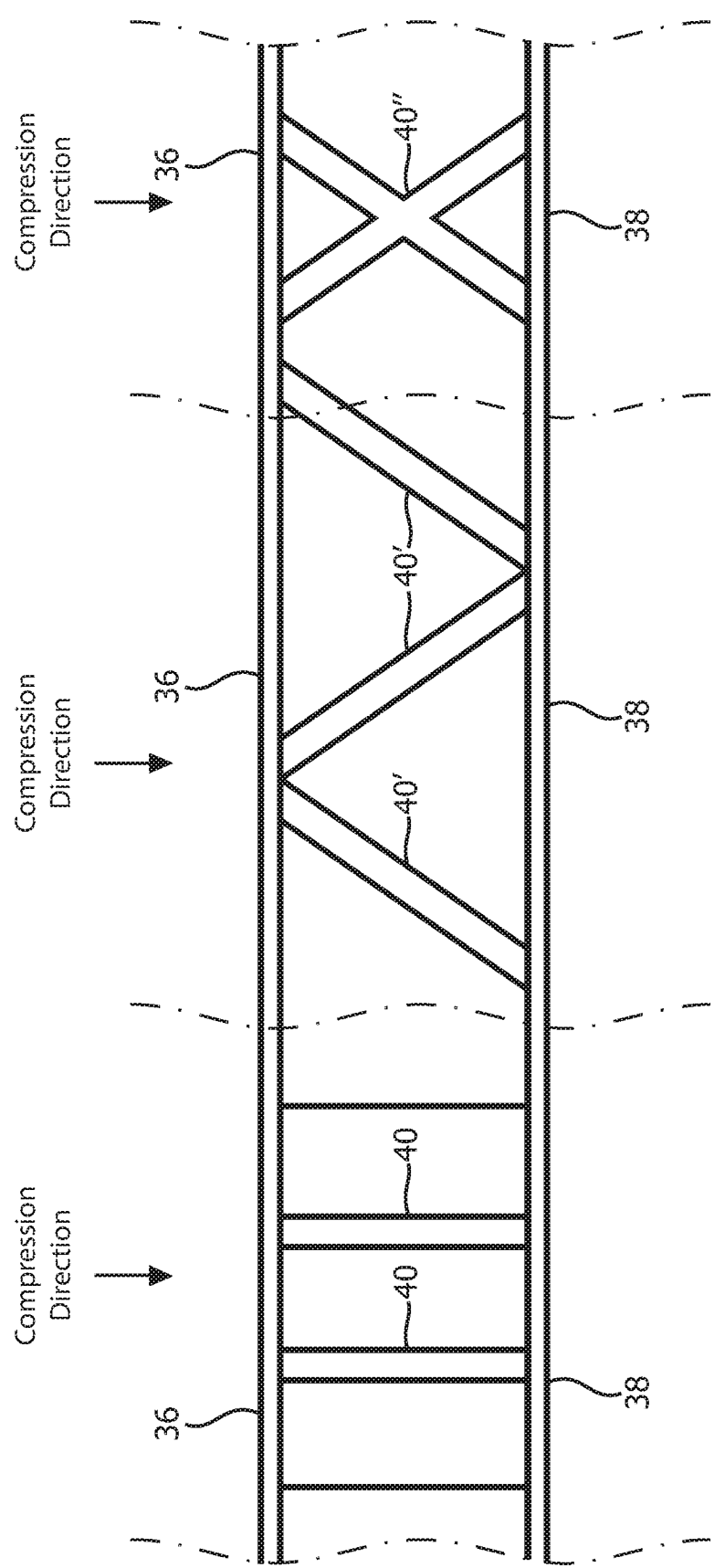
FIG. 20 is a schematic representation showing alternative compression members according to various alternative exemplary embodiments of the disclosed concept.

In still further alternative embodiments, it is possible for the compression members as described herein to be angled with respect to the compression direction as demonstrated in FIG. 20, which shows the compression members 40 of the first embodiment described herein and alternative angled compression members 40' and 40".

Figure 21:
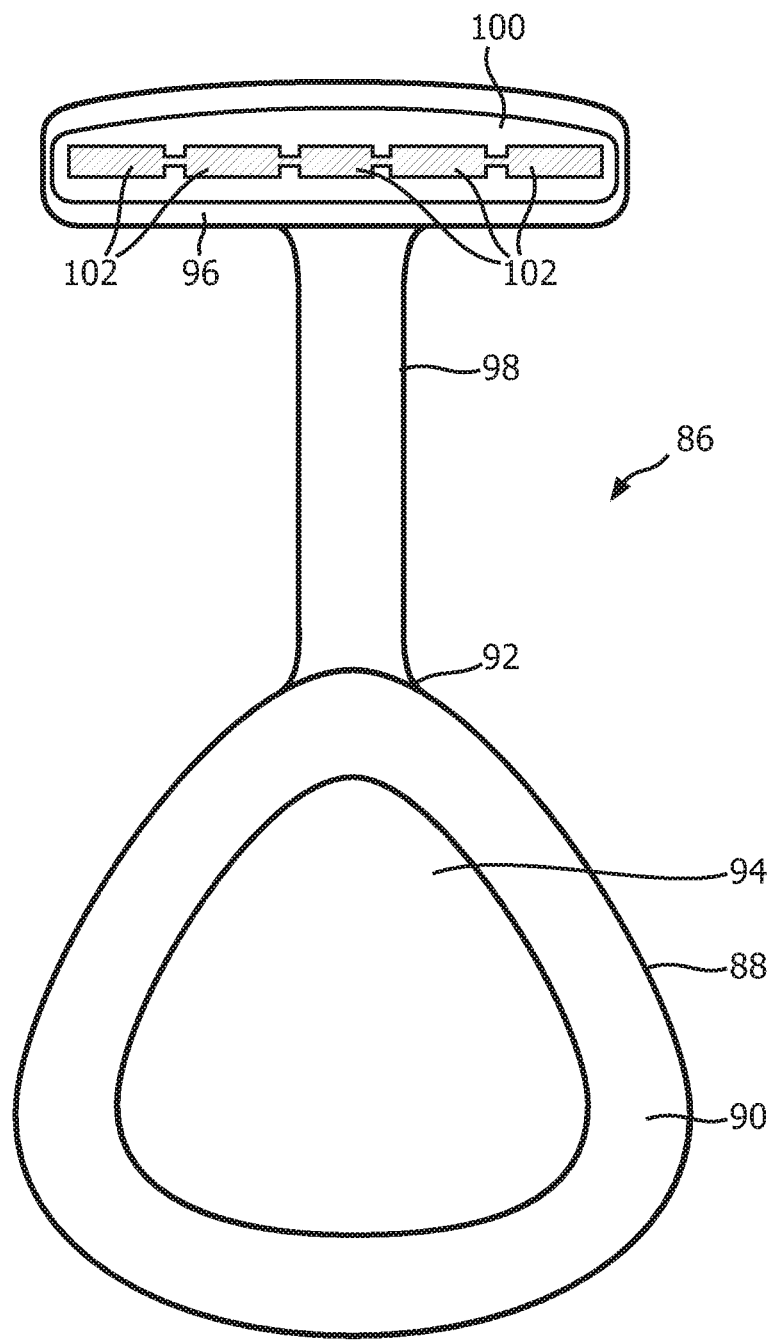
FIG. 21 is a rear elevational view, in partial cross-section, of a patient interface device according to another alternative exemplary embodiment.

FIG. 21 is a rear elevational view, in partial cross-section, of a patient interface device 86 according to another alternative exemplary embodiment. Patient interface device 86 includes a patient sealing assembly 88, which in the illustrated embodiment is a nasal/oral mask. Patient sealing assembly 88 includes a cushion 90 coupled to a frame member 92. Frame member 92 includes a faceplate portion 94 to which cushion 90 is fluidly attached. Frame member 88 also includes a forehead support member 96 that is coupled to faceplate portion 94 by a connecting member 98. A forehead cushion (not shown) is coupled to the rear of forehead support member 96. In addition, a support member 100, similar to support member 20 described herein, is provided between the 4 head cushion and 4 head support member 96. Support member 100 includes compression members 102 which are similar to compression members 40 and which are adapted to local in the manner described herein.

It is also to be understood that the disclosed concept as described herein is not limited to use on or in patient interface devices. Instead, the disclosed concept can be used in combination with any human and/or animal wearables where it is desirable to have contact pressure between the wearable device and the skin. Non-limiting examples of such wearables include, without limitation, a heart rate monitor where the electrodes are strapped against the chest, goggles, e.g., swim goggles and ski goggles, wristwatches, wristbands, jewelry, helmets, saddles, and the like.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A wearable device structured to exert a contact pressure between the wearable device and a skin surface of a wearer, comprising:
    a first member structured to have a first pressure applied thereto;
    a contact member structured to exert the contact pressure against the skin surface in response to the first pressure; and
    a support member positioned between the first member and the contact member, the support member including at least one support member flange and a plurality of compression members extending from the at least one support member flange on a first side of the support member to a second side of the support member opposite the first side of the support member,
    wherein the support member is a unitary member formed separately from the first member and the contact member,
    wherein each of the compression members is structured to buckle in response to a compression force having at least a first predetermined level being applied to the support member,
    wherein the compression members are substantially rectangular in cross-section,
    wherein the wearable device is a patient interface device for delivering a flow of breathing gas to an airway of a patient,
    wherein the first member is structured to receive the flow of breathing gas from a pressure generating device,
    wherein the contact member is a sealing member structured to create a seal against a face of the wearer of the patient interface device,
    wherein each of the compression members is biased to buckle in a direction away from an interior of the patient interface device in response to the compression force having at least a first predetermined level being applied to the support member,
    wherein an end of each compression member is attached to the at least one support member flange at a first connection point between the compression member and the at least one support member flange and a second connection point between the compression member and the at least one support member flange, and
    wherein each first connection point is rounded and each second connection point is square in order to bias the compression member to buckle in the direction away from the interior of the patient interface device.

2. The wearable device according to claim 1, wherein the first member is a face plate member having a main body portion and a flange and the sealing member is a sealing cushion attached to the face plate member, wherein the sealing cushion includes a sealing surface, and wherein the support member is provided between the flange and the sealing surface.

3. The wearable device according to claim 2, wherein the sealing cushion includes a sealing flap coupled to an upper support portion, wherein the sealing surface is provided on the sealing flap, and wherein the support member is provided between the flange and the upper support portion.

4. The wearable device according to claim 1, wherein each of the compression members has a first thickness, wherein the support member includes a plurality of second compression members, wherein each of the second compression members has a second thickness different than the first thickness, and wherein each of the second compression members is structured to buckle in response to a second compression force having at least a second predetermined level being applied to the support member.

5. The wearable device according to claim 1, wherein the compression members are spaced about a perimeter of the support member, and wherein the support member further includes a plurality of webbing members, each webbing member being provided between a respective neighboring pair of the compression members.

6. The wearable device according to claim 1, wherein the support member includes a plurality of second compression members, wherein each of the compression members and the second compression members has a width dimension and a length dimension that is longer than the width dimension, wherein the length dimension of each of the compression members extends in a direction that is substantially perpendicular to a line tangent to an outer perimeter of the support member at the compression member, and the length dimension of each of the second compression members extends in a direction that is substantially parallel to a line tangent to the outer perimeter of the support member at the second compression member.

7. The wearable device according to claim 1, wherein the first member is a main body portion of a pillows style nasal cushion and the sealing member is a nasal prong attached to the main body portion, wherein the nasal prong includes a bottom surface, and wherein the support member is provided between the main body portion and the bottom surface of the nasal prong.

8. The wearable device according to claim 1, wherein the support member is structured such that a longitudinal axis of each of the compression members will be orthogonal to a surface of a face of a patient responsive to the patient interface device being donned by the patient.

9. The wearable device according to claim 1, wherein the support member is made from an elastomeric material.

10. The wearable device according to claim 1, wherein the compression members are spaced along the support member, and wherein the support member further includes a plurality of webbing members, each webbing member being provided between a respective neighboring pair of the compression members.

11. A wearable device structured to exert a contact pressure between the wearable device and a skin surface of a wearer, comprising:

a first member structured to have a first pressure applied thereto;

a contact member structured to exert the contact pressure against the skin surface in response to the first pressure; and a support member positioned between the first member and the contact member, the support member including at least one support member flange and a plurality of compression members extending from the at least one support member flange on a first side of the support member to a second side of the support member opposite the first side of the support member, wherein the support member is a unitary member formed separately from the first member and the contact member, wherein each of the compression members is structured to buckle in response to a compression force having at least a first predetermined level being applied to the support member, wherein the compression members are substantially rectangular in cross-section wherein an end of each compression member is attached to the at least one support member flange at a first connection point between the compression member and the at least one support member flange and a second connection point between the compression member and the at least one support member flange, and wherein each first connection point is rounded and each second connection point is square in order to bias the compression member to buckle in a predetermined direction.

* * * * *